United States Patent
Nagase et al.

(10) Patent No.: US 6,462,230 B1
(45) Date of Patent: *Oct. 8, 2002

(54) METHOD OF AND APPARATUS FOR DECOMPOSING WASTES

(75) Inventors: Yoshiyuki Nagase, Osaka (JP); Ryuichi Fukuzato, Osaka (JP)

(73) Assignees: Kabushiki Kaisha Kobe Seiko Sho, Kobe (JP); Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/633,284

(22) Filed: Aug. 4, 2000

Related U.S. Application Data

(63) Continuation of application No. 08/784,949, filed on Jan. 16, 1997, now Pat. No. 6,255,529.

(51) Int. Cl.⁷ .............................................. C07C 51/06
(52) U.S. Cl. ..................... 562/483; 210/761; 521/45; 562/485; 564/414; 564/497; 568/868; 568/871
(58) Field of Search ................. 210/761, 762, 210/766, 908; 521/42, 45, 48; 540/451, 538; 562/483, 485, 593; 564/497, 498, 414; 568/868, 871

(56) References Cited

U.S. PATENT DOCUMENTS

| | | | |
|---|---|---|---|
| 3,120,561 A | 2/1964 | Chambert | 260/515 |
| 3,128,310 A | 4/1964 | Koch | 260/582 |
| 3,331,876 A | 7/1967 | Van Horn et al. | 260/582 |
| 4,578,510 A | 3/1986 | Doerr | 562/483 |
| 4,605,762 A | 8/1986 | Mandoki | 562/483 |
| 4,620,032 A | 10/1986 | Doerr | 562/483 |
| 4,654,443 A | 3/1987 | Marks et al. | 564/305 |
| 5,386,055 A | 1/1995 | Lee et al. | 562/512.2 |
| 5,457,197 A | 10/1995 | Sifniades et al. | 540/540 |
| 5,473,102 A | 12/1995 | Johnson et al. | 562/483 |
| 5,656,757 A | 8/1997 | Jenczewski et al. | 540/540 |

FOREIGN PATENT DOCUMENTS

| | | |
|---|---|---|
| EP | 0 549 259 | 6/1993 |
| GB | 991387 | 5/1965 |
| GB | 1047101 | 11/1966 |
| WO | WO 93/16976 | 9/1993 |

OTHER PUBLICATIONS

Database WPI, Derwent Publication, AN 93–087972, JP 05 031 000, Feb. 9, 1993.

Chemical Abstracts, vol. 122, No. 26, Jun. 26, 1995, AN 321455.

Patent abstracts of Japan, JP–A–03 500264, Jan. 11, 1991.

Patent Abstracts of Japan, JP–A–58 4735, Jan. 11, 1983.

Patent Abstracts of Japan, JP–A–05 031000, Feb. 9, 1993.

Patent Abstracts of Japan, JP–A–05 271328, Oct. 19, 1993.

*Primary Examiner*—Peter A. Hruskoci
(74) *Attorney, Agent, or Firm*—Oblon, Spivak, McClelland, Maier & Neustadt, P.C.

(57) ABSTRACT

A method of decomposing wastes containing target compounds having one or more of hydrolyzable bonds of ether bond, ester bond, amide bond and isocyanate bond wherein the method comprises continuously supplying the wastes in a molten state or liquid state to a reactor, continuously supplying super-critical water or high pressure/high temperature water to the reactor, bringing the water into contact with the wastes, thereby decomposing the target compounds and then recovering them as raw material compounds or derivatives thereof for the target compounds. Target compounds contained in wastes in chemical plants which could not be utilized but merely incinerated or discarded so far are continuously decomposed into raw material compounds or derivatives thereof for the aimed compound and can be reutilized effectively.

6 Claims, 2 Drawing Sheets

Terephthalic acid recovery rate

Tolylene diamine recovery rate

METHOD OF AND APPARATUS FOR DECOMPOSING WASTES

This application is a Continuation of application Ser. No. 08/784,949 filed on Jan. 16, 1997 now U.S. Pat. No. 6,255,529.

BACKGROUND OF THE INVENTION

1. Field of the Invention

The present invention concerns a method of and an apparatus for decomposing wastes in a chemical plant of decomposing wastes containing by-products formed in a chemical plant by using super-critical or high pressure/high temperature water and capable of recovering and reutilizing raw material compounds or derivatives thereof as an aimed product in a plant from the wastes. More in particular, it relates to a method of and an apparatus for decomposing wastes such as PET bottles and urethane foams by using super-critical water and high pressure/high temperature water and recovering the raw material compounds or the derivatives thereof from the wastes.

2. Description of the Prior Art

In the case of industrially synthesizing various chemical products in chemical plants, it is well-known that by-products other than aimed products are formed or unre-action products remain. For example, in a polymerizing reaction plant, a device for separating a resultant polymer and unreacted monomers in a reaction vessel is essentially provided and the recovered unreacted monomers are generally reutilized as the raw material for the polymerizing reaction. It is also known that oligomers are by-produced in the polymerizing reaction and separation/elimination steps of the oligomers are often conducted since aimed properties can not be obtained or the properties are worsened with lapse of time if the oligomers are left in the polymers. While the unreacted monomers can be reutilized by merely incorporating them again into a raw material feed line, the oligomers are subjected to incineration or discarding since they can not be handled in the same manner as the monomers.

Side reaction products or oligomer such as dimers or trimers of aimed compounds are formed not only in polymerizing reaction plants but also in chemical plants for synthesizing low molecular compounds, and such by-products or oligomers have to be separated from the aimed compounds by, for example, distillation. While by-products can be separated from low molecular materials relatively easily, since separation of the aimed compound from the oligomers is often difficult, a great amount of the oligomers and the aimed compounds are often contained after all in the wastes such as distillation residues. There are scarcely no methods of effectively utilizing such wastes and they are merely subjected to incineration or discarding treatment, which brings about a problem with a view point of resource saving.

In recent years, it has been attempted to detoxicating wastes or obtain utilizable products therefrom by using hydrolyzing or oxidizing reactions in super-critical water or high pressure/high temperature water. For example, Japanese Patent Laid-Open Hei 3-500264 discloses a method of detoxicating wastes in a discharge liquid system by utilizing oxidizing reaction under a super (or sub)-critical state, Japanese Patent Laid-Open Hei 5-31000 discloses a method of hydrolyzing various high molecular compounds by using water at a super-critical or subcritical state and, further, Japanese Patent Publication Hei 3-16328 or Japanese Patent Laid-Open Hei 5-271328 discloses a method of obtaining pure terephthalic acid and glycol from polyethylene terephthalate wastes.

However, although the technique of Japanese Patent Laid-Open Hei 3-500264 is important as a detoxicating method, it involves a problem for the usefulness of the resultant materials since the method accompanies oxidizing reaction and other publications mention nothing about methods and apparatus of efficiently decomposing wastes in chemical plants containing oligomers such as dimers.

OBJECT OF THE INVENTION

In view of the above, in the present invention, wastes in a chemical plant which can not be utilized but are merely incinerated or discarded have been noted and it is an object of the invention to establish a continuous treating method capable of decomposing target compounds such as by-products or oligomers contained in the wastes and decomposing them into raw material compounds or derivatives thereof for aimed compounds in the plant.

SUMMARY OF THE INVENTION

The present invention provides a method of decomposing wastes containing target compounds having one or more of hydrolyzable bonds of ether bond, ester bond, amide bond and isocyanate bond wherein the method comprises continuously supplying wastes in a molten state or a liquid state to a reactor, continuously supplying super-critical water or high pressure/high temperature water to the reactor and bringing the water into contact with the wastes thereby decomposing the target compounds, and recovering them as raw material compounds or derivatives thereof for the target compound.

The present invention further provides an apparatus for decomposing wastes comprising:

a reactor, means for continuously supplying wastes containing target compounds having one or more hydrolyzable bonds of ether bond, ester bond, amide bond and isocyanate bond as they are in a molten state or liquid state to the reactor continuously, means for supplying super-critical water or high pressure/high temperature water to the reactor, and means for introducing a discharged liquid containing decomposition products of the target compounds discharged from the reactor into a separation device.

The decomposing method of the present invention can be applied with no particular restriction to wastes in a chemical plant so long as they contain hydrolyzable target compounds and, among all, the method is applicable effectively when the target compound is "dimer or higher oligomer of raw material compound" as the by-product in a case where the aimed compound in the chemical plant is a high molecular material, or "dimer or higher oligomer of the aimed compound" as by-products in a case where the aimed compound is a low molecular material. By using the decomposing method of the present invention, both "dimer or higher oligomer of raw material compound" and "dimer or higher oligomer of aimed compound" can be decomposed into "raw material compound or derivatives thereof", so that resultant decomposition products can be utilized effectively. "Oligomer" in the present invention means dimer or higher compound with no restriction for the numerical value of the polymerization degree since it varies depending on the kind of the polymer or the polymerizing method.

In the method of the present invention, it is preferred that the super-critical water or high pressure/high temperature water to be supplied to the reactor is set to higher than 100°

C. and higher than 5 MPa, and to supply the supercritical water or high pressure/high temperature water in an equal or more amount based on the weight of the wastes in the chemical plant.

The feature of the decomposing method according to the present invention resides in that the target material is wastes in a chemical plant in a molten state or liquid state and that useful compounds can be recovered continuously from the wastes. Since the wastes in the chemical plant are discharged continuously, s storage vessel for the wastes is necessary in the batchwise treating method. Further, the batchwise process involves a problem that loss of energy is large for cooling or temperature elevation of the reactor upon batch replacement. Further, since a great amount of water is necessary for slurrifying solid-state wastes upon charging them, an energy for putting them to a high temperature is required. In the method according to the present invention, however, since the wastes in the chemical plant can be treated continuously as they are in a molten state or liquid state under constant pressure and temperature conditions, it is free from the foregoing drawbacks and extremely useful in actual operation.

The target to be decomposed in the present invention is wastes in chemical plants containing target compounds having one or more of hydrolyzable bonds of ether bond, ester bond, amide bond and isocyanate bond. When the target compound in the wastes is "dimer or higher oligomer in the raw material compound" as by-products in a case where the aimed compound is a high molecular material or "dimer or higher oligomer of the aimed compound" as by-products in a case where the aimed compound is a low molecular material, wastes can be reutilized particularly effectively by the application of the method of the present invention, so that a great advantages can be provided. In the present specification, "dimer or higher oligomer" is merely referred to as an oligomer.

Among preferred target compounds, those classified as oligomers of raw material compounds can include, for example, polyester oligomers (having ester bond) such as polyethylene terephthalate, polyamide oligomers (having amide bonds) such as nylon and polycarbonate oligomers (having ether bonds). The polyester oligomers include cyclic ester oligomer or chained oligomer which can be decomposed into a dicarboxylic acid such as terephthalic acid and a diol. The nylon oligomers include cyclic or chained oligomers synthesized from $\epsilon$-caprolactom as a raw material and $\epsilon$-amino capronic acid as ring-opened derivative of $\epsilon$-caprolactom can be obtained therefrom. Further, the polycarbonate oligomers can be decomposed into a polyhydric alcohol or polyhydric phenol and carbonic acid as the raw material.

Further, compounds formed by self-polymerization of cyclic ether bond-containing compounds such as epichlorhydrine, ethylene or propylene oxides are oligomers containing ether bonds which may be present both as "oligomer of raw material compound" or as "oligomer of aimed compound". That is, if they are oligomers by-produced upon synthesis of a polymer by using the compounds, they are oligomer of the raw material compound. On the other hand, if they are oligomers by-produced upon synthesis of the compounds, they are oligomers of the aimed compound.

Furthermore, since self-polymerizates having ether bonds are by-produced also upon synthesis of pentaerythritol or like other compound, such oligomers are "oligomer of the aimed compound", which are preferred target compounds in the present invention.

"Oligomer of the aimed compound" can also include those oligomers of compounds such as oligomers of di- or tri-isocyanate compounds (having amide bonds) that cause self reaction and can form hydrolyzable bonds. The isocyanate compound can include, for example, tolylene diisocyanate (2,4- or 2,6-TDI) or diphenyl methane diisocyanate (MDI) and such oligomers are target compounds for decomposition. The compounds obtained after the decomposition are diamine compounds as the intermediate material upon synthesis of isocyanates and they are, for example, tolylene diamine or diphenyl diamino methane.

The present invention is also applicable to by-products which are not oligomers, namely, by-products formed from side reactions of raw materials. In this case, raw material compounds or derivatives thereof can be obtained after decomposition. If an aimed compound and oligomers are less separatable, both of them sometimes may be present mixed together in separably in wastes from the chemical plant. Since the present invention is based on the premise of effectively utilizing the wastes, it is also the feature of the present invention to decompose an aimed compound which can not but be incinerated because of inseparability from other materials into the raw material compound for reutilization. In view of the above, it is also within the scope of the present invention that the aimed compound itself is contained in the target compound. Further, in the present invention, aimed compounds which are obtained in the chemical plant but are discarded as products out of the standards can also be the target compound. Further, when the aimed compound is a high molecular compound, molding products thereof can also be the target compound.

DESCRIPTION OF PREFERRED EMBODIMENTS

A decomposing method in the present invention will be explained more specifically.

Figure 1:
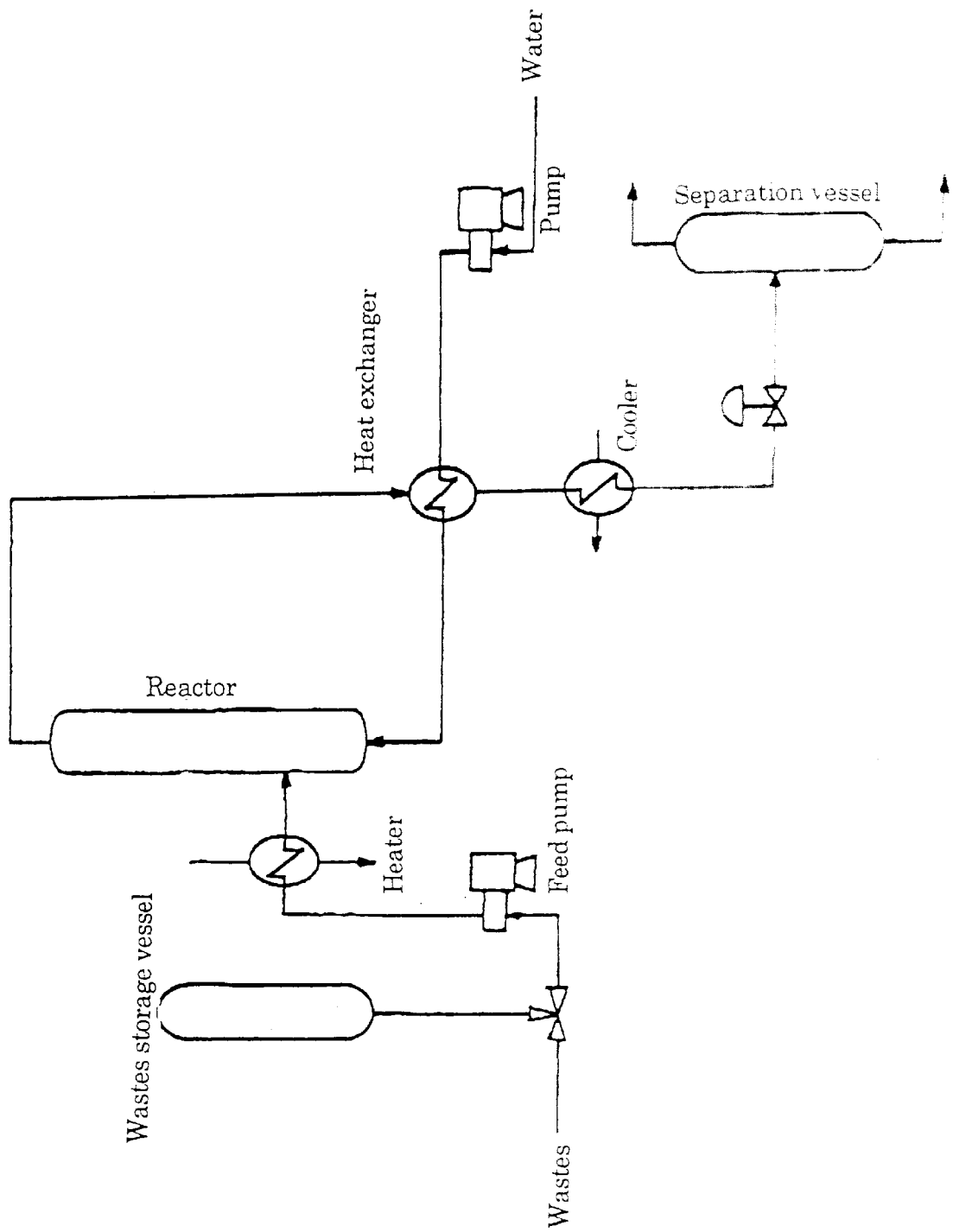
FIG. 1 is a schematic explanatory view illustrating an example of an apparatus for practicing the present invention.

FIG. 1 illustrates an example of a decomposing apparatus system to which the method of the present invention is applied. Wastes to be discarded from a chemical plant are once stored in a storage vessel and then continuously supplied in a molten state or liquid state by a feed pump to a reactor, or such wastes are supplied continuously from the chemical plant directly to the reactor. Direct supply is more preferred since no storage vessel is required. The wastes are in the form of residues from a distillation step in the chemical plant, or in a liquid state after separating a polymer after the polymerizing reaction. If the temperature of the wastes is lower than the temperature for the decomposing reaction, the wastes are introduced while being heated by a heater into the reactor.

On the other hand, super-critical water or high pressure/high temperature water is continuously supplied from a separate line to the reactor. Preferred temperature and pressure conditions for the super-critical water or high pressure/high temperature water are at a temperature of higher than 100° C. and at a pressure of higher than 5 MPa. For decomposing the target compound in the wastes efficiently, it is recommended a temperature higher than 150° C. and a pressure higher than 5 MPa. The upper limit for the temperature is 400° C. and the upper limit for the pressure is 40 MPa. Further, the super-critical water or high pressure/high temperature water is preferably supplied by an equal or more amount based on the weight of the wastes in the chemical plant to be supplied to the reactor. In the method according to the present invention, since the wastes in the liquid state are supplied to the reactor and hydrolyzing reaction can be taken place efficiently, the upper limit for the weight of the super-critical water or high pressure or high temperature water is ten times the weight of the wastes in the reactor and no more amount is necessary for the supply.

In FIG. 1, wastes are supplied from a lower portion of the reactor, while the super-critical water or high pressure/high temperature water is supplied from the bottom of the reactor and both of them are caused to ascend in the reactor. However, this merely shows an example and the design for the positions of introducing the wastes and the super-critical water or high pressure/high temperature water may be properly changed, for example, so as to cause counter current contact depending on the properties of the target compound in the wastes. Further, the reaction time may also be set properly depending, for example, on the amount and the hydrolyzability of the target compound in the wastes and it can be adjusted based on the scale-of the reactor and the feed amount (rate). A discharged liquid discharged from the reactor after the completion of the decomposing reaction is introduced into a separation device. There is no particular restriction for the separation device so long as it adopts a known separation method depending on the resultant decomposition products. It is preferred that a heat exchanger is provided between the separation device and the reactor, by which energy can be used efficiently since heat exchange is conducted between water for forming the super-critical water or high temperature/high pressure water and the discharge liquid discharged at a high temperature.

In the decomposing method and apparatus according to the present invention, since the decomposition is conducted continuously, water for making the wastes into a slurry upon charging them is not required, and there is no loss of energy for cooling and temperature elevation of the reactor upon batch replacement as in the batchwise process. Further, since the wastes in the chemical plant can be treated continuously as they are in the molten state or liquid state under constant conditions, it is extremely useful for actual operation.

EXAMPLE

The present invention will be explained more specifically by way of examples but the present invention is not restricted by the following examples and all of modifications or changes practiced within a scope not departing the spirit of the present invention are contained in the technical range of the invention.

Example 1

Figure 2:
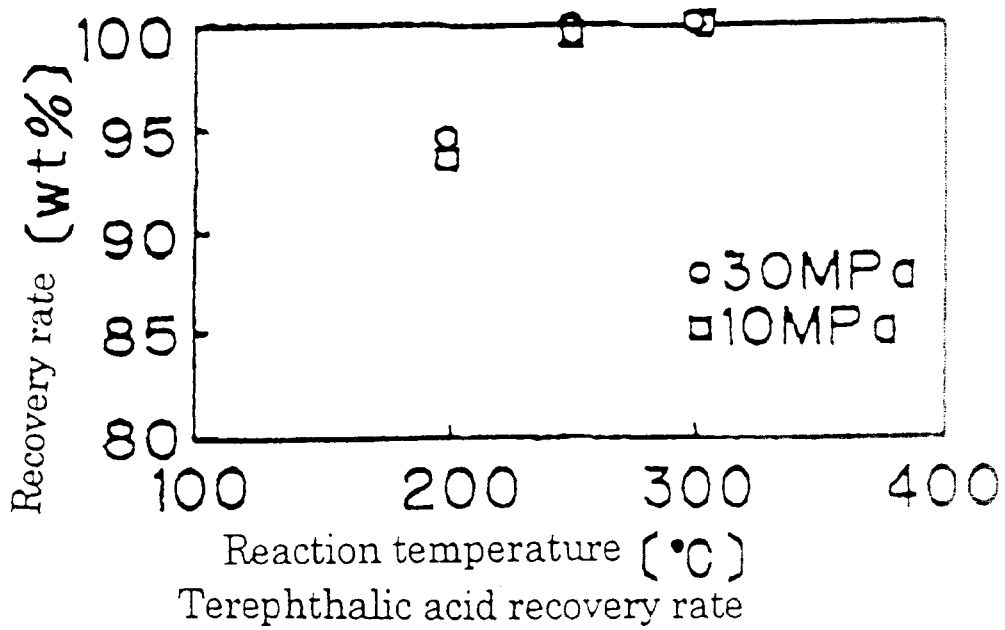
FIG. 2 is a graph illustrating a recovery rate of terephthalic acid from PET oligomer.

A decomposition treatment for PET oligomers by-produced in a chemical plant for producing polyethylene terephthalate (PET) was conducted under the conditions shown in Table 1. Products formed by the decomposition are terephthalic acid and ethylene glycol. Table 1 and FIG. 2 show the recovery rate of terephthalic acid in each of experiments. The recovery rate is given on the basis of weight percent of the recovered terephthalic acid to the weight of the resultant terephthalic acid calculated theoretically from the weight of the charged PET oligomers. As can be seen from FIG. 2, 100% recovery rate was obtained at a temperature higher than 250° C. under both of pressures at 10 MPa and 30 MPa.

TABLE 1

| Experiment No. | 1 | 2 | 3 | 4 | 5 | 6 |
|---|---|---|---|---|---|---|
| Reaction temperature (° C.) | 200 | 250 | 300 | 200 | 250 | 300 |
| Reaction pressure (MPa) | 30 | 30 | 30 | 10 | 10 | 10 |
| Hydrolysis ratio* | 5 | 5 | 5 | 5 | 5 | 5 |
| Reaction time (min) | 30 | 30 | 30 | 30 | 30 | 30 |
| Recovery rate (%) | 94.8 | 100 | 100 | 93.9 | 99.6 | 100 |

*"Hydrolysis ratio" is: high pressure/high temperature water weight/waste weight in the reactor Example 2

An experiment for the recovery of tolylene diamine as an intermediate material for TDI was conducted by using distillation residues discarded in a chemical plant-for the synthesis of tolylene diisocyanate (TDI). Experimental conditions are shown in Table 2. The contents of the distillation residues are 40 wt % of TDI, 20 wt % of TDI dimer and 40 wt % of TDI trimer. The distillation residues contain a great amount of TDI as the aimed compound, because the oligomers and TDI are less separatable by distillation. However, since TDI is also decomposed into tolylene diamine, all of the decomposing products (diamine compounds) obtained can be utilized again as the intermediate material for the process for the isocyanate synthesis process.

Figure 3:
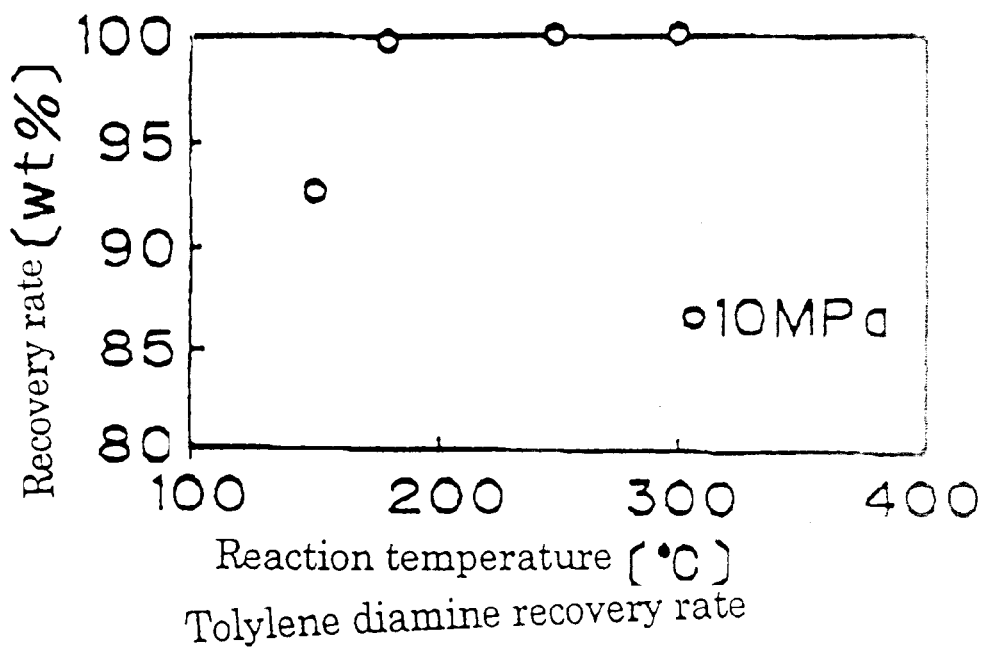
FIG. 3 is a graph illustrating a recovery rate of tolylene diamine from distillation residues formed in a TDI synthesis process.

Table 2 and FIG. 3 show the recovery rate of tolylene diamine in each of the experiments. The recovery rate is based on the weight percent of the recovered tolylene diamine to the weight of the resultant tolylene diamine theoretically calculated based on the weight of the charged distillation residues. As can be seen from FIG. 3, 100% recovery rate was obtained at a temperature higher than 180° C.

TABLE 2

| Experiment No. | 1 | 2 | 3 | 4 |
|---|---|---|---|---|
| Reaction temperature (° C.) | 150 | 180 | 250 | 300 |
| Reaction pressure (MPa) | 10 | 10 | 10 | 10 |
| Hydrolysis ratio* | 5 | 5 | 5 | 5 |
| Reaction time (min) | 10 | 10 | 10 | 10 |
| Recovery rate (%) | 92.8 | 99.6 | 100 | 100 |

*"Hydrolysis ratio" is: high pressure/high temperature water weight/waste weight in the reactor According to the method and apparatus of the present invention, wastes which could not be utilized but were merely incinerated or discarded can be utilized effectively. Since the wastes can be decomposed continuously by the method according to the present invention, water for making the wastes into the slurry upon charging them is not required and there is no loss of energy for cooling and temperature elevation of the reactor upon batch replacement as in the batchwise process, it is possible to provide a method and an apparatus which are extremely useful in view of actual operation capable of continuously processing wastes as they are in the molten state or liquid state under constant conditions.

What is claimed is:

1. A method of recovering one or more monomeric compounds from a waste material comprising:

supplying said waste material to a reactor;

continuously supplying a hydrolyzing reactant consisting essentially of water at a temperature higher than 100° C. and at a pressure higher than 5 MPa to said reactor;

decomposing said waste material by hydrolyzing hydrolyzable bonds thereof with said hydrolyzing reactant in said reactor, and recovering said one or more monomeric compounds;

wherein said waste material contains hydrolyzable bonds selected from the group consisting of ether bonds, ester bonds, amide bonds and isocyanate bonds, and both of said waste material and said water are caused to flow in substantially the same direction in said reactor, wherein said decomposing said waste material by hydrolyzing hydrolyzable bonds thereof with said hydrolyzing reactant is carried out under substantially constant pressure and temperature conditions in said reactor.

2. The method of claim 1, additionally comprising conducting heat exchange between a hydrolyzed product discharged from said reactor and said hydrolyzing reagent to heat said water to said temperature.

3. The method of claim 1, wherein said water is supplied in an equal or greater amount based on the weight of said waste material.

4. The method of claim 1, wherein said waste material is an oligomer.

5. The method of claim 1, wherein at least 90% wt. of said waste material is decomposed and recovered as said one or more monomeric compounds.

6. The method of claim 1, wherein both of said waste material and said water are caused to flow in an ascendant direction in said reactor.

* * * * *

UNITED STATES PATENT AND TRADEMARK OFFICE
CERTIFICATE OF CORRECTION

PATENT NO. : 6,462,230 B1  Page 1 of 1
DATED : October 8, 2002
INVENTOR(S) : Yoshiyuki Nagase et al.

It is certified that error appears in the above-identified patent and that said Letters Patent is hereby corrected as shown below:

<u>Title page,</u>
Item [73], Assignee, should read:

-- [73]  Assignees:  Kabushiki Kaisha Kobe Seiko Sho, Kobe (JP); Mitsui Takeda Chemicals Inc., Tokyo (JP) --

Signed and Sealed this

Twentieth Day of May, 2003

JAMES E. ROGAN
*Director of the United States Patent and Trademark Office*